United States Patent [19]
Brindle

[11] Patent Number: 5,405,666
[45] Date of Patent: * Apr. 11, 1995

[54] FLEXIBLE ELASTOMERIC ARTICLE WITH ENHANCED LUBRICITY

[75] Inventor: Philip W. Brindle, Ely, England

[73] Assignee: LRC Products Ltd., London, England

[*] Notice: The portion of the term of this patent subsequent to Mar. 7, 2012 has been disclaimed.

[21] Appl. No.: 178,579

[22] Filed: Jan. 7, 1994

Related U.S. Application Data

[63] Continuation-in-part of Ser. No. 2,785, Jan. 8, 1993.

[51] Int. Cl.$^6$ .............................................. A41D 19/00
[52] U.S. Cl. .................................. 428/36.4; 428/323; 428/339; 428/147; 428/149; 2/168
[58] Field of Search .................... 428/35.7, 36.4, 36.8, 428/36.9, 331, 339, 323, 147, 149

[56] References Cited

U.S. PATENT DOCUMENTS

| | | |
|---|---|---|
| 2,273,995 | 2/1942 | Rogerson et al. . |
| 2,976,576 | 3/1961 | Wichterle et al. . |
| 3,072,914 | 1/1963 | Velonis et al. . |
| 3,326,742 | 6/1967 | Shepherd . |
| 3,585,103 | 6/1971 | Thomson . |
| 3,607,433 | 9/1971 | Isenberg et al. . |
| 3,745,042 | 7/1973 | Lim et al. . |
| 3,813,695 | 6/1974 | Podell, Jr. et al. . |
| 3,856,561 | 12/1974 | Esemplare et al. . |
| 3,872,515 | 3/1975 | Miner et al. . |
| 3,901,755 | 8/1975 | Martin et al. . |
| 3,925,138 | 12/1975 | Shaul et al. . |
| 3,930,076 | 12/1975 | Kliment . |
| 3,940,533 | 2/1976 | Arsac . |
| 3,966,530 | 6/1976 | Cutts et al. . |
| 4,024,317 | 5/1977 | Stoye et al. . |
| 4,070,713 | 1/1978 | Stockum . |
| 4,110,495 | 8/1978 | Carter et al. . |
| 4,125,477 | 11/1978 | Tani et al. . |
| 4,143,109 | 3/1979 | Stockum . |
| 4,302,852 | 12/1981 | Joung . |
| 4,499,154 | 2/1985 | James et al. . |
| 4,548,844 | 10/1985 | Podell et al. . |
| 4,575,476 | 3/1986 | Podell et al. . |
| 5,102,741 | 4/1992 | Miyabayashi . |

FOREIGN PATENT DOCUMENTS

| | | |
|---|---|---|
| 0543657A1 | 5/1993 | European Pat. Off. . |
| 859297 | 1/1961 | United Kingdom . |
| 1028446 | 5/1966 | United Kingdom . |
| 1541155 | 3/1976 | United Kingdom . |
| WO88/08311 | 11/1988 | WIPO . |
| WO90/00890 | 2/1990 | WIPO . |

OTHER PUBLICATIONS

Romberg, "Aqueous Chlorination of Natural Rubber Surfaces", A.C.S. Rubber Division, Spring Meeting 1986.
T.C.Q. Noakes, Proc. Int. Rubb. Technol. Conf., Penang, Malaysia 1988.
Natural Rubber Technical Information Sheet No. 17, The Malaysian Rubber Producers' Research Association, Latex Series 1977.
D. C. Blackley, "High Polymer Latices", Palmerton Publishing Company, p. 548, 1966.
M. W. Philpott, J. Rubb. Res. Inst. Malaya. 22(5):441–449, 1969 (Compounding Natural Rubber Latex for Improved Performance).

*Primary Examiner*—James J. Seidleck
*Assistant Examiner*—Patrick R. Delaney
*Attorney, Agent, or Firm*—Darby & Darby

[57] ABSTRACT

This invention relates to elastomeric flexible articles (e.g., film articles) that exhibit enhanced lubricity ("slip") with respect to both dry and damp surfaces, particularly skin or other tissue of the wearer, as compared to similar articles or films that are not treated as described herein. This invention also relates to processes for making such articles or films.

37 Claims, 8 Drawing Sheets

FIG. I
SURFACE SCALE: 57mm = 100 um

FIG. 2
SURFACE SCALE: 70 mm = 100 um

FIG. 3 SURFACE SCALE; 31mm = 10 μm

FIG. 4
SURFACE SCALE: 60mm = 10um

FIG. 5
SURFACE SCALE : 15mm = 10um

FIG. 6
SURFACE SCALE: 23mm = 100um

FIG. 7
SURFACE SCALE: 47mm = 10um

FIG. 8
SURFACE SCALE : 54mm = 10μm

FLEXIBLE ELASTOMERIC ARTICLE WITH ENHANCED LUBRICITY

FIELD OF THE INVENTION

This application is a Continuation-In-Part application of U.S. patent application Ser. No. 08/002,785 filed on Jan. 8, 1993 and allowed May 15, 1994.

This invention relates to elastomeric flexible articles (e.g., film articles) that exhibit enhanced lubricity ("slip") with respect to both dry and damp surfaces, particularly skin or other tissue of the wearer, as compared to similar articles or films that are not treated as described herein. This invention also relates to processes for making such articles or films.

BACKGROUND OF THE INVENTION

Elastomeric surfaces of articles, in general, exhibit poor lubricity with respect to a dry surface, such as dry skin or other mammalian tissue. These properties are due to surface friction. Additionally, many elastomeric articles or surfaces display poor lubricity with respect to damp surfaces.

A high surface friction coefficient is useful for many applications such as tire treads, flooring and footwear. However, these same properties are a distinct disadvantage in many other applications and especially in those applications wherein an elastomeric surface must slide on another surface, such as in the donning of gloves over dry or damp skin. This is particularly important in the use of medical gloves, such as examination gloves and surgeon's gloves. These gloves are relatively close-fitting in order to provide sensitivity. Furthermore, most surgeons don their gloves after scrubbing up and without having fully dried their hands, so that areas of their hands may be dry while other areas may be distinctly damp. Consequently, the elastomeric materials useful in such applications must exhibit concurrently enhanced lubricity with respect to dry surfaces (dry slip), enhanced lubricity with respect to damp surfaces (damp slip), as well as the requisite mechanical properties (flexibility, strength, etc.).

Conventionally, dry slip is achieved by the use of powder lubricants such as magnesium carbonate, starch and talc. However, if the hands are damp, the use of a powder is counter-productive and may actually inhibit donning. Furthermore, in surgery, there is a risk of loose powder contaminating the surgical field. These materials can also cause irritation and may be allergenic.

Chlorination of rubber has also been proposed for the purpose of reducing tackiness and decreasing the coefficient of friction of rubber. (See Romberg, "Aqueous Chlorination of Natural Rubber Surfaces", A.C.S. Rubber Division, Spring Meeting (1986); T.C.Q. Noakes, Proc. Int. Rubb. Technol. Conf., Penang, Malaysia (1988); Natural Rubber Technical Information Sheet No. 17, The Malaysian Rubber Producers' Research Association, Latex Series (1977); D.C. Blackley, "High Polymer Lattices", Palmerton Publishing Company (1966), p. 548, and PCT/GB92/00171, published as WO 92 13497. However, chlorination can adversely affect the mechanical properties of flexible elastomeric articles such as rubber gloves and is better avoided for this reason. In addition, chlorination produces surfaces which have very poor damp slip.

Polymeric lubricant coatings which are bonded to the tissue-contacting glove surface or are embedded in the rubber itself have been proposed for the purpose of reducing surface friction of rubber in, for example, U.S. Pat. Nos. 3,813,695; 3,856,561; 4,070,713; 4,143,109; and 4,302,852. U.S. Pat. No. 3,813,695, in particular, describes a laminated surgical glove having a flexible outer layer and a hydrophilic plastic (hydrogel polymer) inner layer. Other articles such as catheters and bathing caps coated with hydrophilic polymers are described in U.S. Pat. Nos. 3,326,742; 3,585,103; 3,607,433; 3,745,042; 3,901,755; 3,925,138; 3,930,076; 3,940,533; 3,966,530; 4,024,317; 4,110,495; and 4,125,477 as well as British Patent Publication Nos. 1028446 and 859297.

James et al., U.S. Pat. Nos. 4,499,154 and 4,575,476, describe treating a rubber article having a coating of a lubricated hydrogel polymer (inherently providing dry slip) bonded layer, with a surfactant material, such as a quaternary ammonium cationic surfactant, or a long chain fatty amine material to improve the lubricity of the coating with respect to damp skin.

U.S. Pat. Nos. 4,143,109 and 4,070,713, and British Patent 1,541,155, propose the use on the skin-contacting surface of an elastomeric medical glove of a second layer of elastomeric material bearing partially-embedded particulate matter (cross-linked starch particles or polyethylene, or ethylene-vinyl acetate copolymer particles 5–40 microns in size). The elastomeric material forming the second layer is said to adhere to both the particles and the elastomeric glove substrate. Carboxylated styrene-butadiene latex, brominated butyl rubber and styrene-polyethylene/butylene-styrene block copolymer are disclosed as specific elastomeric materials suitable for use in forming the particle-bearing layer. The patents state that (i) the elastomeric substrate can be 125–175 microns thick; (ii) the inner layer can be 5–30 microns thick; and (iii) the particle size should be greater than the thickness of the second layer. In all the examples, however, the layer is 15 microns thick, i.e. 10% of the thickness of the laminated glove and 37.5–300% of the thickness of the particles. The resulting gloves are said to be donned easily without the use of additional lubricants, such as dusting powder. The particles described all appear to be organic, solid, essentially nonporous particles. Moreover, as far as the present inventors know, the gloves described in these patents have never been commercialized despite a felt need in the art for powder-free gloves.

European Patent Application EP 543,657 published May 26, 1993 discloses powder-free elastomeric medical gloves comprising a layer of an antiblocking composition (serving as a binder) with particles distributed throughout. The majority of the particles must have a size greater than the thickness of the antiblocking composition in the layer. The antiblocking composition should have mechanical properties comparable to those of the elastomer substrate. Polyurethane aqueous dispersion is said to be preferred as the binder. The particles can be cross-linked corn starch, nylon, polyurethane or mixtures and should be of a size range between 5 and 50 μm with an average size between 30 and 40 μm. This EP application does not disclose nor suggest the requirement that specific properties of the particles or the binder be present or have values within specified ranges that would result in good dry and wet slip as well as good adhesion to the substrate.

It has now been discovered that the dry slip and the damp slip properties of elastomeric articles can be improved substantially by providing on the wearer-contacting surface of these articles a thin layer of an adhering binder material bearing porous, absorbent microparticles and subsequently applying a surfactant or a long chain fatty amine. Under a scanning electron microscope the microparticles appear to be coated by the binder even though they are partially protruding therefrom to give a microroughened (globular reticulated) appearance to the coating, as depicted for example in FIG. 1.

SUMMARY OF THE INVENTION

Disclosed are flexible elastomeric articles displaying slip properties with respect to damp and dry mammalian tissue comprising on their wearer-contacting surface a thin coating of an adherent binder material compatible with the elastomer, the binder being bonded to said surface and appearing to envelop preferably substantially nonaggregated microparticles. The particles are randomly distributed on the wearer-contacting surface and appear coated with the binder, preferably they protrude partially from the binder surface and give the coating a substantially microroughened appearance. The coated article is then treated with a surfactant or a long-chain fatty amine.

Suitable particles include those having a mean size within the range of 4-20 (and preferably 5-13) microns, an oil absorption higher than about 80 g of oil per 100 g of microparticles and preferably a binder:particle weight ratio greater than 1:1. The coating constitutes preferably no more than about 5% of the thickness of the article.

Preferred materials include polyurethane or natural rubber as the substrate elastomer for the article. Suitable binders have a glass-transition temperature within the range from about −60° to about +30° C. Preferred binders comprise at least one of a vinyl acetate-ethylene copolymer, a vinyl acetate-ethylene acrylate copolymer, a vinyl acetate-ethylene-vinyl chloride terpolymer or a polyurethane (which may be the same as or different from the substrate). Preferred microparticles are silica, polyamide or cellulose triacetate particles having a size within the range of about 5 to about 13 microns and a relatively narrow size distribution. Preferably, the particles have a substantially regular shape without sharp angles or edges and are in substantially nonaggregated form (e.g., are primary particles of a near-spherical shape). Preferred surfactants are amphoteric and cationic surfactants.

The elastomeric flexible articles include, without limitation, surgical and examination gloves.

BRIEF DESCRIPTION OF THE DRAWINGS

The invention is further described by the following figures, which are intended to illustrate it without limiting its scope.

DETAILED DESCRIPTION OF TEE INVENTION

The invention envisages flexible elastomeric articles including those adapted for use in partial or total contact with mammalian tissue, such as surgical, examination and dental gloves, condoms, bandages, catheters, ureters, sheaths, and sheath-type incontinence devices and other film articles. Furthermore, the damp/dry slip-conferring materials may be provided on one or more surfaces of the article including, but not limited to, an inner and/or an outer surface relative to the wearer, as appropriate under the circumstances of the use of each article.

For purposes of this description, the outer surface of an article and, in particular, a glove, is defined as that surface which becomes an external surface of the glove in the position of actual use when worn. The inner surface is defined as that surface which is adjacent to the skin of the wearer when worn. The reverse is true in the case of a catheter or ureter: the outer surface is the surface in contact with the wearer's tissue. To avoid ambiguity, the term "wearer-contacting" surface will be used herein. "Tissue" includes skin or epithelia without limitation.

In the present invention, the substrate elastomer of the elastomeric flexible articles may be a natural or synthetic rubber. Without limitation, examples of synthetic rubbers are polyurethane, polyacrylate, polybutylene, and silicone rubbers and block copolymers of monomers such as styrene and butadiene. Polyurethane and natural rubber are preferred, with polyurethane being most preferred. Typical thicknesses of the elastomer substrate for surgical gloves are within the range 30 to 200 microns, without limitation, with 100-150 microns being preferred.

Figure 5:
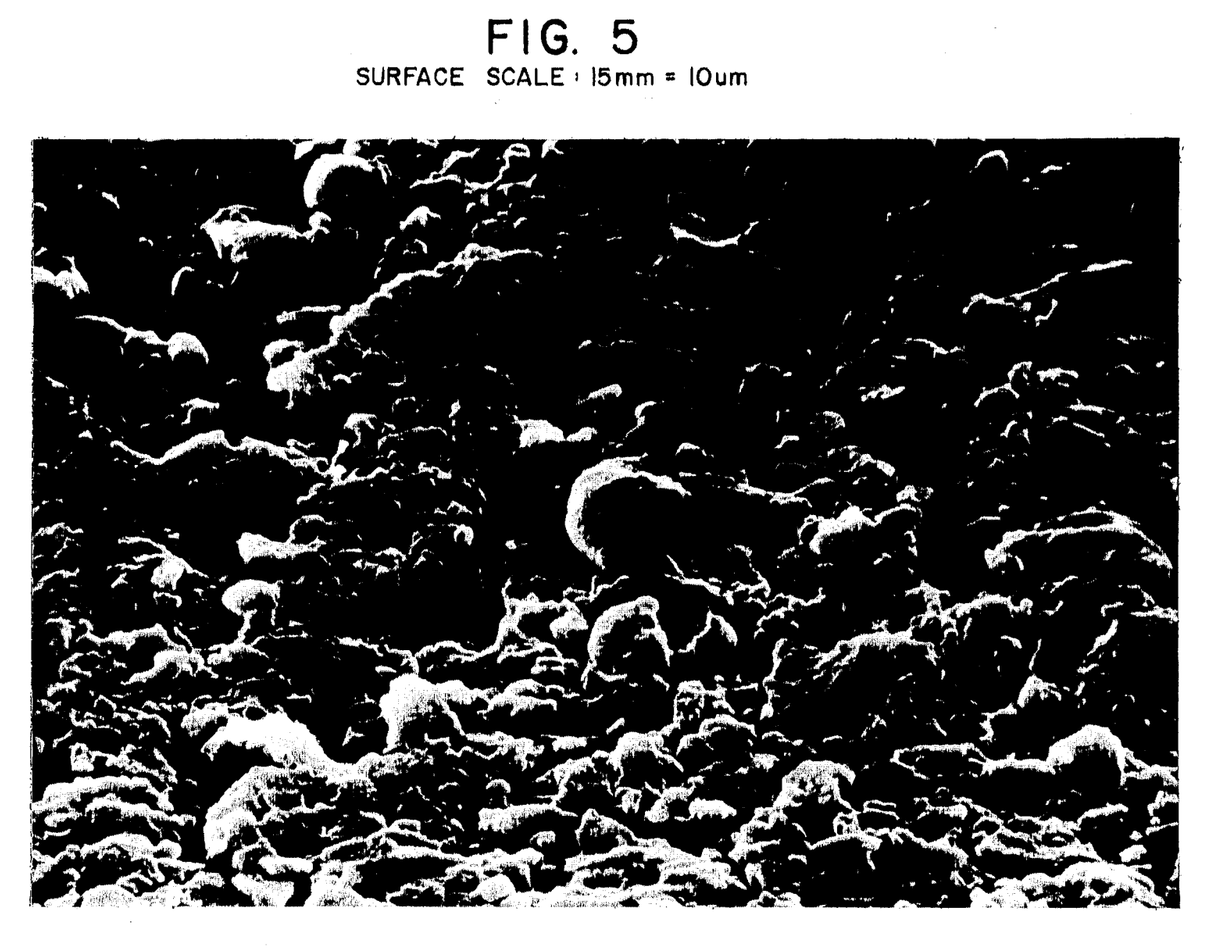
FIG. 5 is the same type of photomicrograph as FIG. 1 showing a binder layer containing corn starch microparticles according to the prior art. Noteworthy is the presence of cracks and disruptions throughout the surface.

The material used for the binder should have good adhesion to both the elastomeric substrate and to the microparticles and should preferably not adversely affect the mechanical properties of the article. Moreover, the binder layer should be resistant to the conditions of article manufacture and use. Clearly, the choice of the binder will depend, in substantial measure, on the nature of the substrate elastomer and of the microparticles. We have found, however, that by limiting the thickness of the coating relative to the thickness of the substrate and using correspondingly small, porous, absorbent microparticles, a variety of binder materials can be used. Although it is possible to obtain adequate dry-slip properties using a thicker coating and/or one that shows poor adhesion to the substrate (as deduced, for example, by the presence of a multitude of microscopic cracks in the surface—see FIG. 5), this is not desirable because such a coating shows a tendency to break up to some extent on deformation of the article (such as is incident to normal use, e.g., during donning in the case of a glove) and therefore suffers from the same disadvantages as use of powder lubricants.

When the substrate is a polyurethane and the microparticles are silica (which are preferred), the glass transition temperature of the binder polymer should be in the range of about −60° to about +30° C., preferably between about −5° and about +15° C. Preferred binder materials for a polyurethane substrate include polyurethanes, as well as copolymers and terpolymers of vinyl acetate (e.g., with ethylene, with ethylene acrylate, with ethylene and vinyl chloride, etc.).

When the substrate is natural rubber and the microparticles are silica, the glass transition temperature of the binder polymer should be in the range of about −60° to about +30° C., preferably between about −15° and about +5° C. Preferred binder materials for a natural rubber substrate include copolymers and terpolymers of vinyl acetate (e.g., with ethylene, with ethylene acrylate, with ethylene and vinyl chloride, etc.).

Preferably, the microparticles are absorbent, substantially nonaggregated microspheres, preferably made of silica (or alternatively of polyamide or cellulose triacetate) having a mean size within the range from about 4 to about 20 microns (preferably with at least about 55% and most preferably at least about 60% of the particles being within the above size range). Particle size was measured on a weight percent basis (Coulter Counter, Industrial D Model) and/or on a volume percent basis (Malvern Master Sizer Model E, Malvern Ltd.).

It is further preferred that at least about 30% of the particles are within the 5–13 micron range. (Percentage distribution in the foregoing sentence is on a volume percent basis.) Obviously, the narrower the size distribution the better. Also, a unimodal distribution is preferred.

As revealed by scanning electron micrographs, the particles appear to be enveloped by the binder and the binder-plus-particle (i.e. the coating) thickness should preferably not exceed about 5% of the substrate thickness, and most preferably should not exceed about 2–3% of the substrate thickness.

Microparticle porosity can be conveniently measured in terms of oil absorption (e.g., DIN ISO 787/V). Microparticles having oil absorption values higher than about 80 g/100 g (and preferably higher than about 180 g/100 g) and being substantially smooth (e.g., approximately spherical), in shape and substantially nonaggregated are suitable for the purpose of the invention, but those having oil absorption values higher than about 280 g/100 g are most preferred. Examples of preferred silicas are Syloid ED5 and Syloid ED80, supplied by W. R. Grace & Co. The pore volume should be preferably in the range 1 to 2 ml/g. By "substantially nonaggregated" we mean that at least a substantial majority of the particles are primary particles, not aggregates of smaller particles.

A binder:microparticle ratio sufficient to confer dry slip properties to a glove (or other article according to the invention) is for example within the range of greater than about 1:1 (preferably about 2:1) to about 5:1 by weight based on the binder composition. For medical gloves, a ratio of 3:1 is most preferred. It will be appreciated by those skilled in the art that this amount is subject to optimization for a particular article according to the invention. In other words, minimum and maximum binder:particle ratio is expected to vary somewhat (and the optimum binder:particle ratio is also expected to vary), depending on (i) the application to which the flexible elastomeric article is adapted and (ii) the composition of the elastomeric article. In light of the present disclosure, however, this is within the skill of the art.

The surfactant used to endow the wearer-contacting surface with damp slip may be any surfactant which is suitable for use on skin or other tissue and does not cause an allergic, irritant, or other undesirable reaction in said skin or other tissue. Thus, in principle, amphoteric, anionic, cationic, and nonionic surfactants, and long-chain fatty amines can be used, as taught for example in various patents and patent applications recited herein, the disclosure of which is incorporated by reference in its entirety as if it were physically present in the present specification. However, in general, nonionic surfactants are found to be less effective than the other types and are not recommended as a class (although individual members of this class may be quite effective). Anionic surfactants, namely, those comprising at least one lipophilic moiety such as an alkyl, aralkyl, aryl, or cycloalkyl group containing 8 to 18 carbon atoms, and a hydrophilic moiety such as a carboxylic, phosphoric, sulfonic, sulfuric, or other acid group or salt thereof, generally provide adequate damp slip properties but such surfactants are not preferred as a class because they show a marked tendency to cause irritation to skin and tissue at concentrations effective to provide damp slip.

Suitable cationic surfactants include those comprising at least one lipophilic moiety such as an alkyl, aralkyl, aryl, or cycloalkyl group containing 6 to 18 carbon atoms, and a hydrophilic moiety such as a substituted ammonium group (for example, a tetra-alkylammonium, pyridinium, or like group). The counter-ion present should be compatible with the tissue of the wearer; it could be, for example, chloride or other halide.

Preferred cationic surfactants are quaternary ammonium compounds having at least one $C_8$–$C_{18}$ hydrocarbyl (alkyl, aryl, aralkyl or cycloalkyl) group; a preferred hydrocarbyl group is a hexadecyl group. The hydrocarbyl group may be attached to a quaternary nitrogen atom which is part of a heterocyclic ring (such as a pyridine, morpholine, or imidazoline ring).

Most preferred cationic surfactants are benzalkonium chlorides, hexadecyltrimethylammonium chloride, hexadecylpyridinium chloride, dodecylpyridinium chloride, the corresponding bromides, and a hydroxyethyl-heptadecylimidazolium halide.

Suitable amphoteric surfactants include: betaines and sulteines containing at least one $C_6$–$C_8$ hydrocarbyl group. Other types of suitable surfactants are amine oxides, sulfosuccinates and isothionates containing at least one $C_6$–$C_{18}$ hydrocarbyl group. Amphoteric surfactants are preferred because they generally have a low skin irritancy potential.

Mixtures of surfactants may also be used.

A particularly preferred surfactant is hexadecyl pyridinium chloride, other particularly preferred surfactants are coconut alkyldimethylammonium betaine and coco aminopropyl betaine, all of which are commercially available.

In a preferred embodiment, the surfactant is bacteriocidal or bacteriostatic. The use of such a surfactant serves to inhibit bacterial growth when the layer formed on the coating is in contact with the skin or tissue of the wearer. This is especially an advantage for surgeon's gloves because they are sometimes punctured during surgical procedures, and any bacteria which may have grown on a surgeon's skin since commencement of the operation may be released into the surgical field.

When a neutral fatty amine is used, a $C_6$–$C_{18}$ hydrocarbyl group, such as a hexadecyl group, is preferably attached to the nitrogen atom. Such an amine is N-N-dimethylhexadecylamine.

The coating of surfactant or long chain fatty amine need not coat the wearer-contacting surface completely. It is only necessary that enough surfactant or long-chain amine is applied to enhance damp slip. It is preferred, to the extent that it is practicable, to keep the surfactant on the wearer-contacting surface, in the case of medical or dental gloves, in order to ensure that maximum grip is maintained on the outer surface. The surfactant can be applied as an aqueous solution containing from about 0.2 to about 2% surfactant. The article can be dipped in such solution or the solution can be sprayed or painted on it, preferably before it is removed from the former. Alternatively, the surfactant can be applied after the article is stripped from the former.

The process for applying the particle-containing coating to the wearer-contacting surface of the elastomeric substrate depends, in part, on the nature of the substrate and on whether the glove or other article is formed by dipping a former into a elastomeric polymer latex or into a solution of the elastomeric polymer in a suitable solvent. Methods for making the elastomeric substrate articles of the present invention are well-known in the art.

Where the article is formed from compounded natural rubber latex, the deposit on the former is beaded and leached in the normal way and may then be partially or fully dried but not fully vulcanized. It is envisaged that the coating will normally be applied by subsequently dipping the deposit on the former into an aqueous suspension of the coating material, i.e., the binder and microparticles. The deposit and coating may then be heated to dry them and to complete vulcanization of the rubber.

In some cases, it may be advantageous to spray or paint a suspension or solution of the coating material on to the deposit on the former. Where spraying is used, it may be convenient to spray the rubber deposit first with a suspension or solution of the binder, dry the deposit, spray with a suspension of the microparticles, dry again, and spray once more with the binder and carrier, followed by final drying and vulcanization.

Other substrate polymers in dispersed, e.g. latex, form, including polyurethanes, may be treated similarly, although a vulcanizing step will not be needed in every case, as can be readily appreciated by those skilled in the art.

When the article is formed by dipping from a polymer in solution, for example, a polyurethane in tetrahydrofuran, the deposit on the former is partially freed from solvent by heating and is then dipped into an aqueous suspension of the coating material and dried in the manner already described. In this case, also, the coating may be applied by spraying or painting, rather than dipping.

It is understood that various optional ingredients may be incorporated in these articles as apparent to those skilled in the art. For example, where the article is a glove an antiblock agent may be used which would facilitate donning and use. The antiblock agent is preferably a low-melting wax (mp. from about 100° C. to about 150° C.) such as polyethylene wax added as an aqueous emulsion (e.g., 1–2%) to the coating mixture. The particle size of the wax should be preferably less than 1 μm to avoid interference with the surface morphology.

DESCRIPTION OF THE PREFERRED EMBODIMENTS

In the following examples, which illustrate the invention without limiting its scope, the following product designations are used:

FK383 precipitated silica (Trade Mark of Degussa Ltd.)

Sipernat 50S precipitated silica (Trade Mark of Degussa Ltd.)

Silosiv A10 zeolite (Trade Mark of W. R. Grace & Co.)

Syloid AL1 silica (Trade Mark of W. R. Grace & Co.)

Syloid ED2 silica (Trade Mark of W. R. Grace & Co.)

Syloid ED5 silica (Trade Mark of W. R. Grace a Co.)

Syloid ED80 silica (Trade Mark of W. R. Grace & Co.)

Syloid 622 silica (Trade Mark of W. R. Grace & Co.)

Vinamul 3692 vinyl acetate/ethylene acrylate copolymer (Trade Mark of Vinamul Ltd. Carshalton, Surrey, England).

Vinamul 3231 vinyl acetate/ethylene copolymer (Trade Mark of Vinamul Ltd.)

Vinamul 3452 vinyl acetate/ethylene/vinyl chloride terpolymer (Trade Mark of Vinamul Ltd.)

Vinamul 3459 vinyl acetate/ethylene/vinyl chloride terpolymer (Trade Mark of Vinamul Ltd.)

Estane 5707 polyurethane (Trademark of B. F. Goodrich Inc.)

Witcobond 787 polyurethane aqueous emulsion (Trademark of Witco Chemical Corporation, New York, N.Y.)

21P40 carboxylated styrene butadiene rubber (Trademark of Doverstrand Ltd., Harlow, Essex, England)

Dehyton AB30 amphoteric surfactant (coconut alkyldimethylammonium betaine, Trade Mark of Henkel Ltd.)

Cross-linked corn starch was from Tunnel Refineries, Greenwich, London, U.K.

Non Cross-linked corn starch was from Biosorb, Arbrook/Ethicon, U.K.

Aquaslip 655 or 671 polyethylene emulsion (Capricorn Chemicals, Ely, Cambridgeshire, U.K.)

HK 125/400 (Degussa)

Dehydol TA 20, nonionic surfactant (Henkel Ltd.)

Witcobond 769 Aqueous Polyurethane (Witco)

Doverstrand 76D41, self-crosslinked styrene butadiene latex (Doverstrand)

Kraton D1117 styrene-isoprene-styrene block copolymer (Shell Chemicals, U.K.)

0.5% Solid wax (A671)

DC 193 silicone surfactants (Dow Corning, Reading, U.K.)

Microthene FN510 Polyethylene powder (Croxton and Garry, Dorking U.K.)

Microthene FE 532 ethylenevinylacetate powder (Croxton and Garry, Dorking U.K.)

Orgasol 2002 UD Polyamide powder (Atochem, Newbury, U.K.)

Orgasol 2002 EXD Polyamide powder (Atochem, Newbury, U.K.)

TA25 Cellulose triacetate (Presperse Inc., South Plainfield, N.J., U.S.A.)

Beetle 9040 aqueous polyurethane (BIP Chemicals Ltd., Oldbury, U.K.)

Laurapal X1207 non-ionic Surfactant (Witco)

Antioxidant 2246 (2,2'-Methylenebis (4- methyl-6-t-butylphenol) (Anchor Chemical (U.K.) Ltd., Clayton, Manchester, U.K.)

The characteristics of finished films or articles were determined as follows:

Tensile strength, breaking elongation (EB), and stress at 100% strain (S100) were measured according to ASTMD412. Tear strength was measured on angle test pieces (ASTMD624).

Adhesion of the binder to the substrate and adhesion of the particles to the binder were assessed visually using a scanning electron microscope (magnification $1.5 \times 10^2$ to $2.5 \times 10^3$). The samples were evaluated visually based, respectively, on the presence and frequency of cracks in the coating and on "crater" formation in the coating (the latter indicating that particles had been dislodged and therefore did not adhere to the binder). They were then rated on an arbitrary scale from 1 to 5 with 1 signifying "excellent" and 3 signifying "barely acceptable."

Dry slip and damp slip were evaluated subjectively on a scale of 1 (excellent slip) to 5 (no slip—undonnable in the case of a glove) with 3 being "barely acceptable".

EXAMPLE 1

A film article (glove) was made by dipping a hand-shaped former into an 18% solution of a polyurethane in tetrahydrofuran (single dip process). While in the wet gel state (partially dried), and still on the former, the article was dipped into an aqueous coating solution containing 2.0% silica microparticles (Syloid ED5), 6.0% vinyl acetate/ethylene acrylate copolymer (Vinamul 3692; Tg +13° .), 0.1% xanthan gum, and 91.9% deionized water (all percentages being by weight). It was dried for 20 minutes at 100° C. While still on the former, the dried glove was dipped into a 0.75% aqueous solution of an amphoteric surfactant (Dehyton AB30) for 10 minutes. It was then stripped from the former and air-dried. The thickness of the coating in this Example was about 5 microns; the thickness of the binder alone was 4–5 microns.

Figure 1:
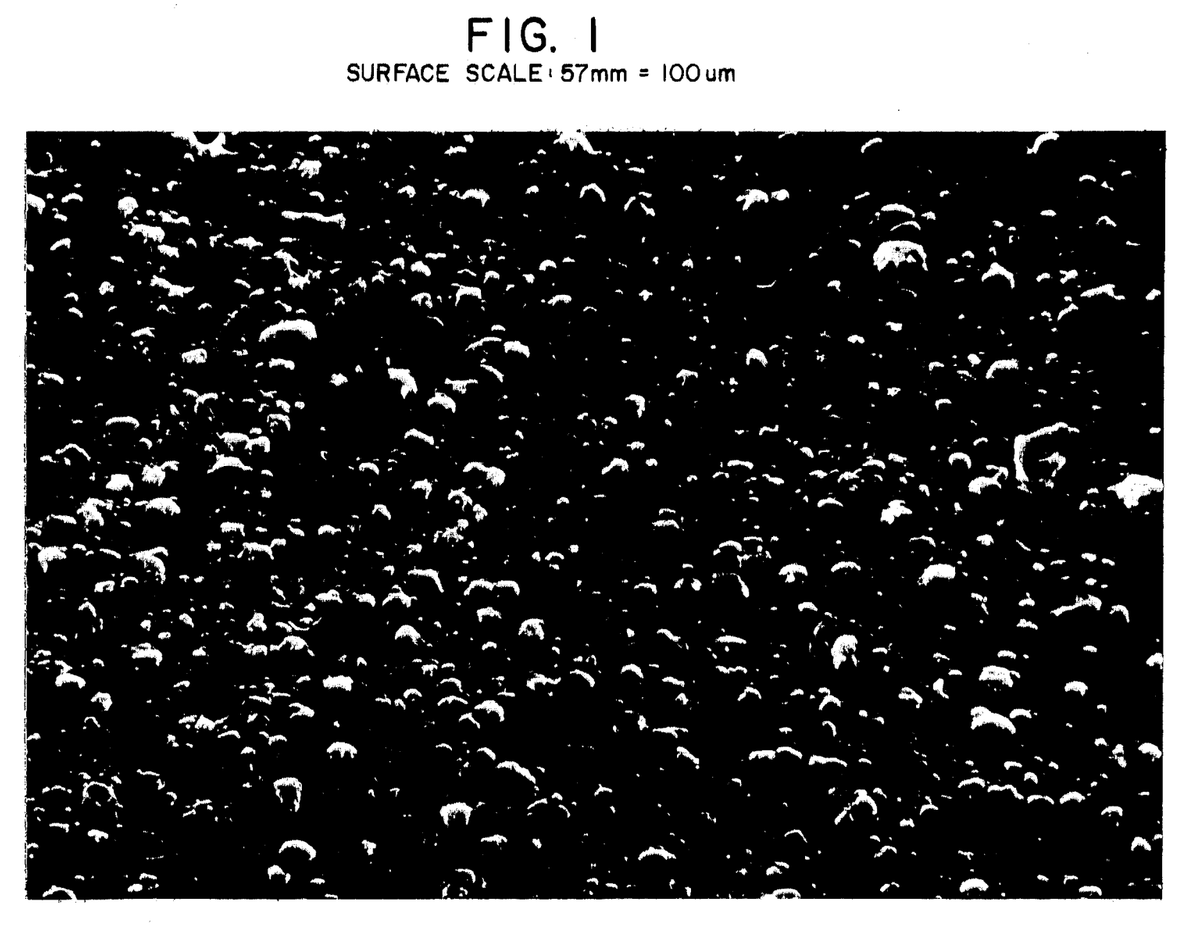
FIG. 1 is a photomicrograph taken through a scanning electron microscope (SEM) showing the microparticle-bearing binder layer of a preferred embodiment of the present invention. Noteworthy is that the coating has a substantially smooth yet microroughened appearance essentially free of sharp angles, cracks and craters.

The finished glove had tensile strength 60.3MPa and tear strength 60.1N/mm, compared with 62.9MPa and 59.6N/mm respectively, for a similarly prepared but uncoated glove. Its dry slip rating was 1 and its damp slip rating 2.5. Excellent adhesion of the coating to the polyurethane (as well as of the particles to the binder) was demonstrated by scanning electron microscopy which showed a microroughened surface containing no cracks of the coating, no free fragments, and no craters (FIG. 1).

EXAMPLES 2–6

Coated polyurethane gloves were prepared as in Example 1 except that the Vinamul 3692 was substituted by one of the binders shown in Table 1, which shows the dry slip rating and degree of adhesion achieved in each case.

TABLE 1

| | ADHESION OF VARIOUS BINDERS TO THE POLYURETHANE SUBSTRATE | | |
|---|---|---|---|
| Example No. | Binder | Tg (°C.) | Adhesion |
| 2 | Vinamul 3231 | 0 | 1 |
| 3 | Vinamul 3459 | 21 | 2 |
| 4 | Vinamul 3452 | 30 | 3 |
| 5 | Witcobond 787 | −50 | 1 |
| 6 | Estane 5707 | about −40 | 1 |

EXAMPLES 7–13

Coated polyurethane gloves were prepared as in Example 1 except that the Syloid ED5 was substituted by one of the microparticles listed in Table 2below. The dry slip ratings and degrees of adhesion achieved in each case are set forth in Table 2. The mean diameters in Table 2 were measured by Coulter counter and are based on weight percent; the oil absorption values were as specified by the manufacturer (except for Example 13). Compare Table 2A where mean diameters were also measured by Malvern (based on volume percent) and oil absorption values were determined by the inventor.

TABLE 2

| | EFFECT OF VARIOUS MICROPARTICLES ON PROPERTIES OF POLYURETHANE GLOVES | | | | | |
|---|---|---|---|---|---|---|
| Ex. No. | Particle Type | Mean Diameter | Pore Volume ml/g | Oil Adsorption g/100 g | Dry Slip | SEM |
| 1 | Syloid ED5 | 5 μm | 1.8 | 320 | 1 | FIG. 1 |
| 7 | Syloid ED80 | 8 μm | 1.8 | 300 | 1 | |
| 8 | Syloid 622 | 12 μm | 1.2 | 180 | 1.5 | |
| 9 | Syloid ED2 | 2 μm | 1.8 | 320 | 2.5 | |
| 10 | FK383 | 1–2 μm | N/A | 220 | 3 | FIG. 2 |
| 11 | Syloid AL1 | 8 μm | 0.4 | 80 | 3 | FIG. 3 |
| 12 | Sipernat 50S | 8 μm | N/A | 330 | 3.5 | |
| 13 | Corn Starch (Cross-linked) | 5–40 μm | N/A | 58 | 2–3 | FIG. 4 |

Figure 2:
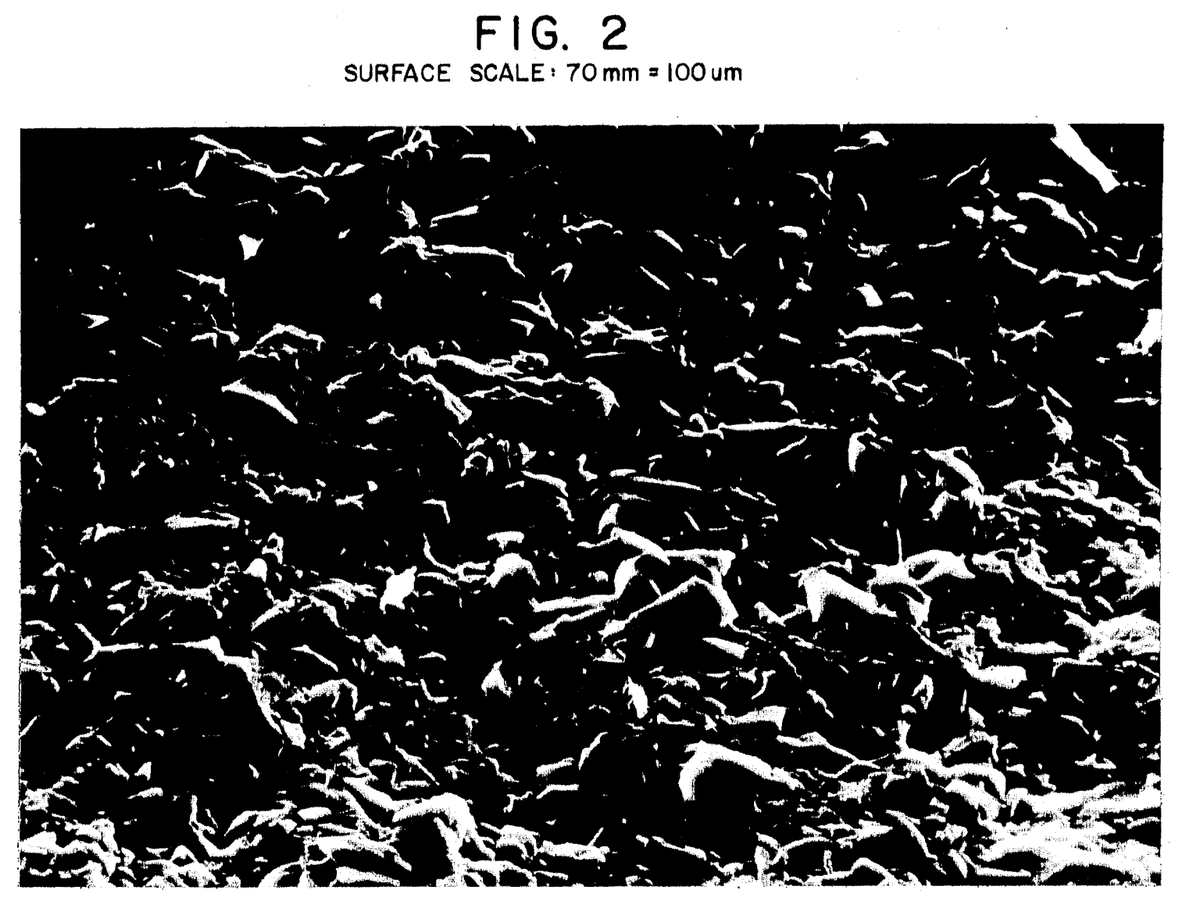
FIG. 2 is the same type of photomicrograph as FIG. 1 wherein the binder layer contains microparticles of a different type and presents sharp angles.
Figure 3:
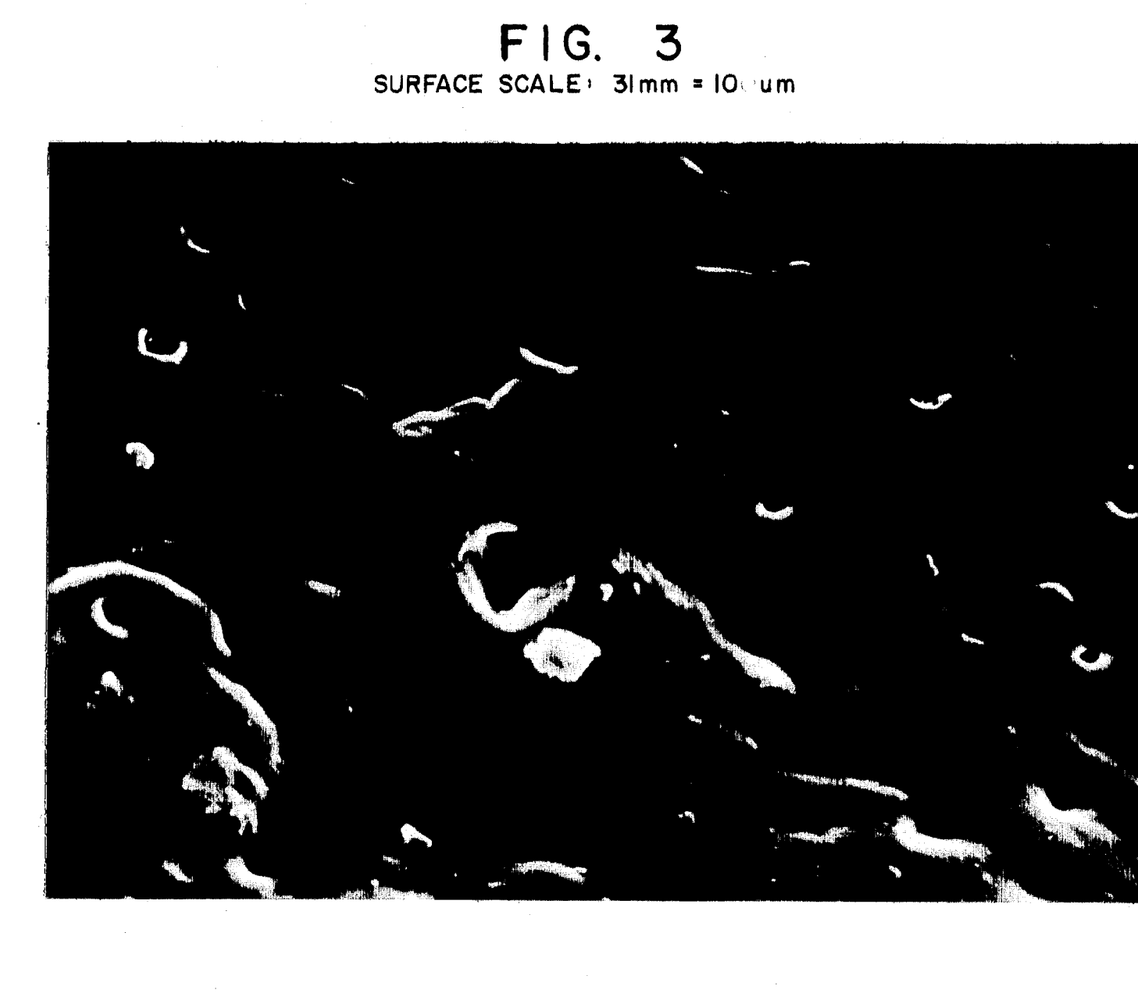
FIG. 3 is the same type of photomicrograph as FIG. 1 containing microparticles of yet a different type and presenting a "cratered" surface.
Figure 7:
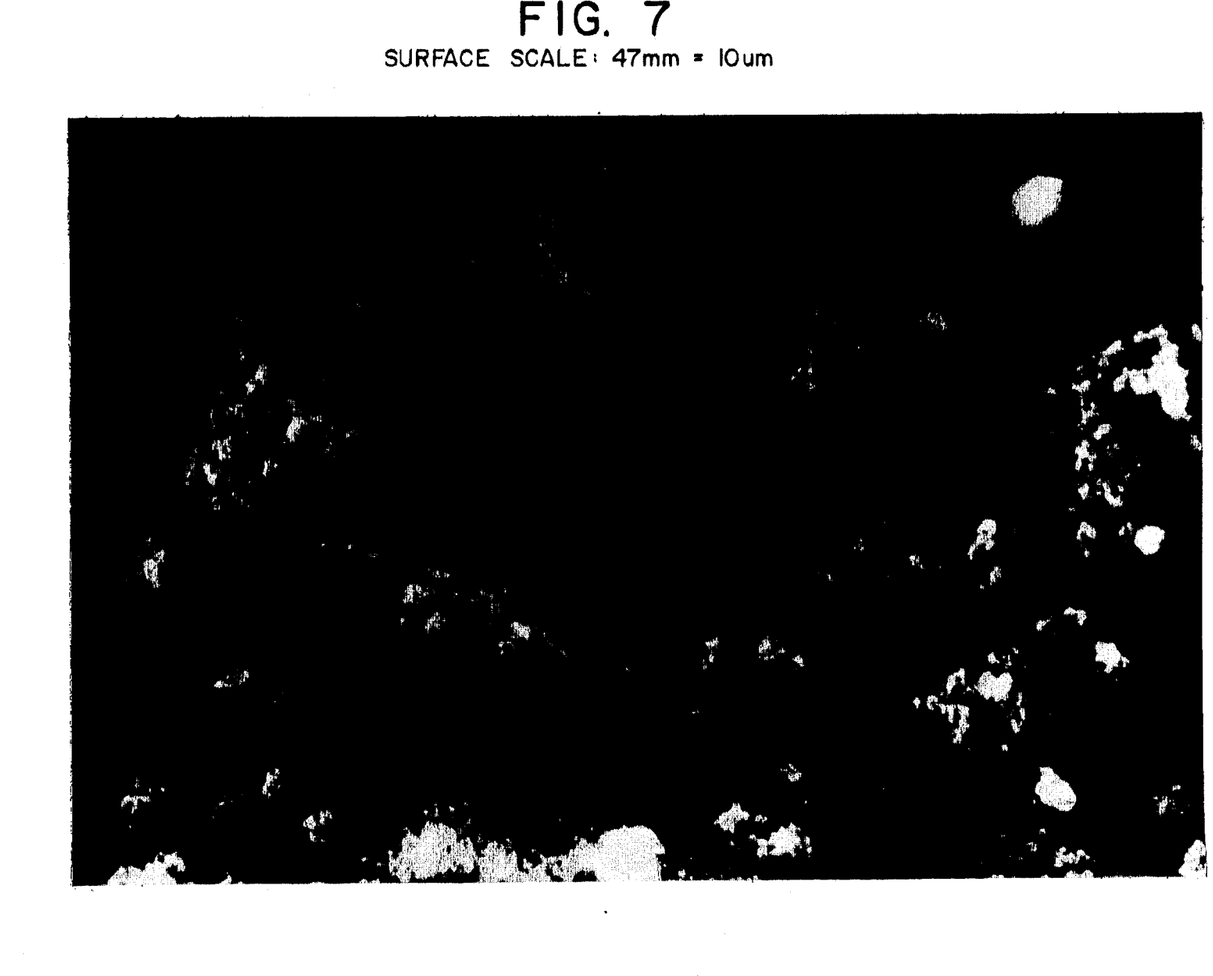
FIGS. 7 and 8 are the same type of photomicrograph as FIG. 1 and depict the substantially aggregated nature of precipitated silica particles FK 383 and HK125, respectively.

As can be seen from Table 2, the particles in Examples 1, 7 and 8 performed most satisfactorily. Particles of Example 9 were too small. Particles of Example 10 were aggregated as seen in FIG. 7 (and consequently not of substantially smooth shape) and this may account for the highly angular appearance of the resulting coating (FIG. 2). In Example 11 the particles had insufficient oil absorption and yielded a coating with craters indicating dislodging of particles (FIG. 3). In Example 12, particle size range and distribution were broad (for example, particles as large as 50μm and as small as 1 μm were routinely seen on SEM and the proportion of 8μm particles was relatively small), and this accounts for the poor slip properties of the coating (see also Example 12A).

Figure 4:
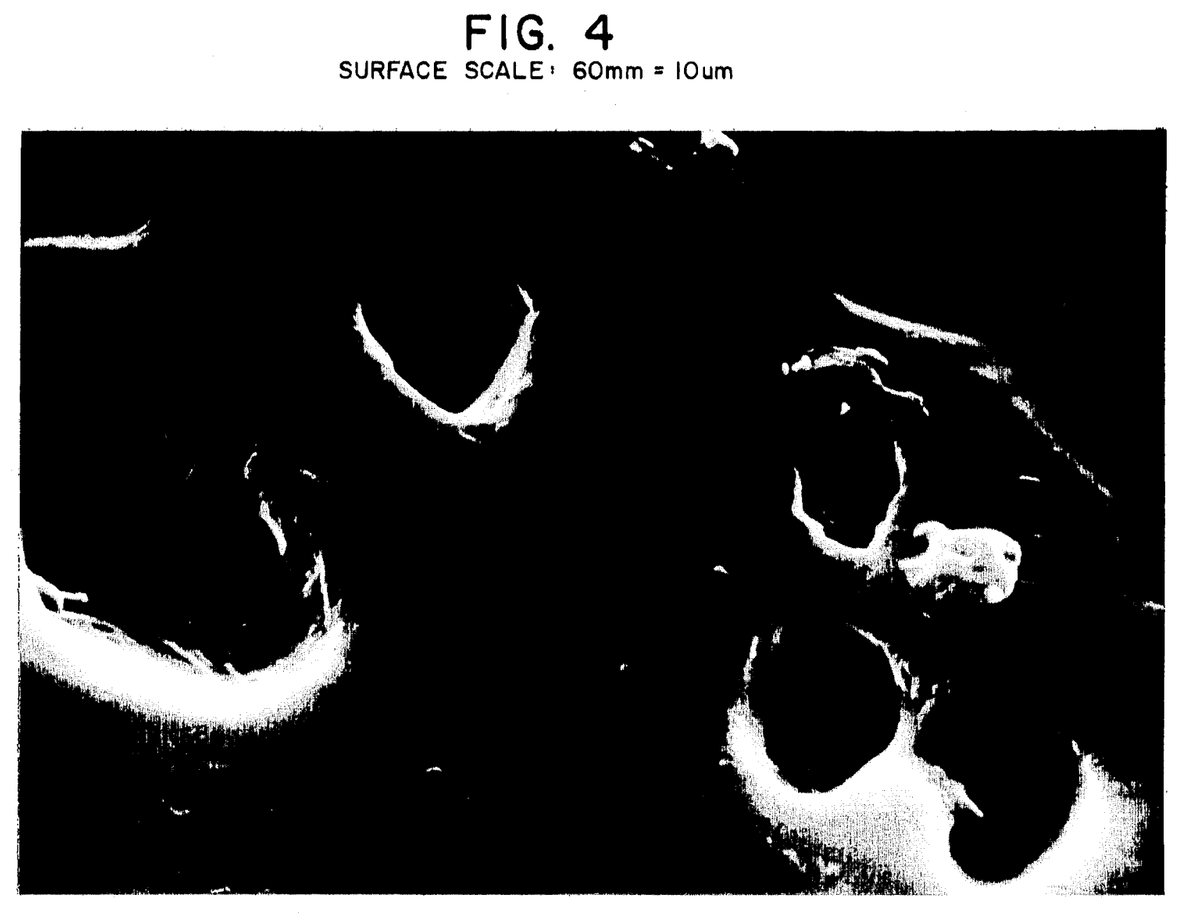
FIG. 4 is the same type of photomicrograph as FIG. 1 showing a coating containing another type of microparticles and also presenting a cratered surface.

The corn starch particles in Example 13 also yielded a coating with craters indicating that the particles had become dislodged (FIG. 4). Their oil absorption was also poor.

EXAMPLE 14

Comparison Example

Coated polyurethane gloves were prepared as in Example 1 except that the aqueous coating dispersion contained 1.5% crosslinked corn starch, 7.5% 21P40, 0.005% xanthan gum, 0.6% casein, 0.4% zinc oxide, and 90.0% deionized water, (according to U.S. Pat. No. 4,143,109) and the dried glove was dipped into deionized water (no surfactant) for 10 minutes prior to stripping. The finished glove had satisfactory physical properties but its dry slip rating was 2–3. Adhesion of the coating to the substrate was poor, judged by its extensively cracked appearance (FIG. 5) and the fact that much of the coating had become detached during the water treatment prior to stripping. The finished glove had the appearance and feel of a powdered glove.

EXAMPLES 15–16

A glove was made from high-ammonia natural rubber latex by a procedure known to those skilled in the art and involving the steps of dipping a hand-shaped former into an aqueous coagulant, air-drying, and dipping into the latex. The wet gel deposit was then dipped into one of the coating dispersions described in Examples 1 and 2. It was then dried and vulcanized by heating for ½ hour at 120° C. The properties of the finished gloves are described in Table 3.

TABLE 3
EFFECT OF VARIOUS COATINGS ON THE PROPERTIES OF NATURAL RUBBER GLOVES

| Example No. | Coating of Example No. | Dry Slip | Adhesion |
|---|---|---|---|
| 15 | 1 | 2 | 3 |
| 16 | 2 | 2 | 1 |

Figure 6:
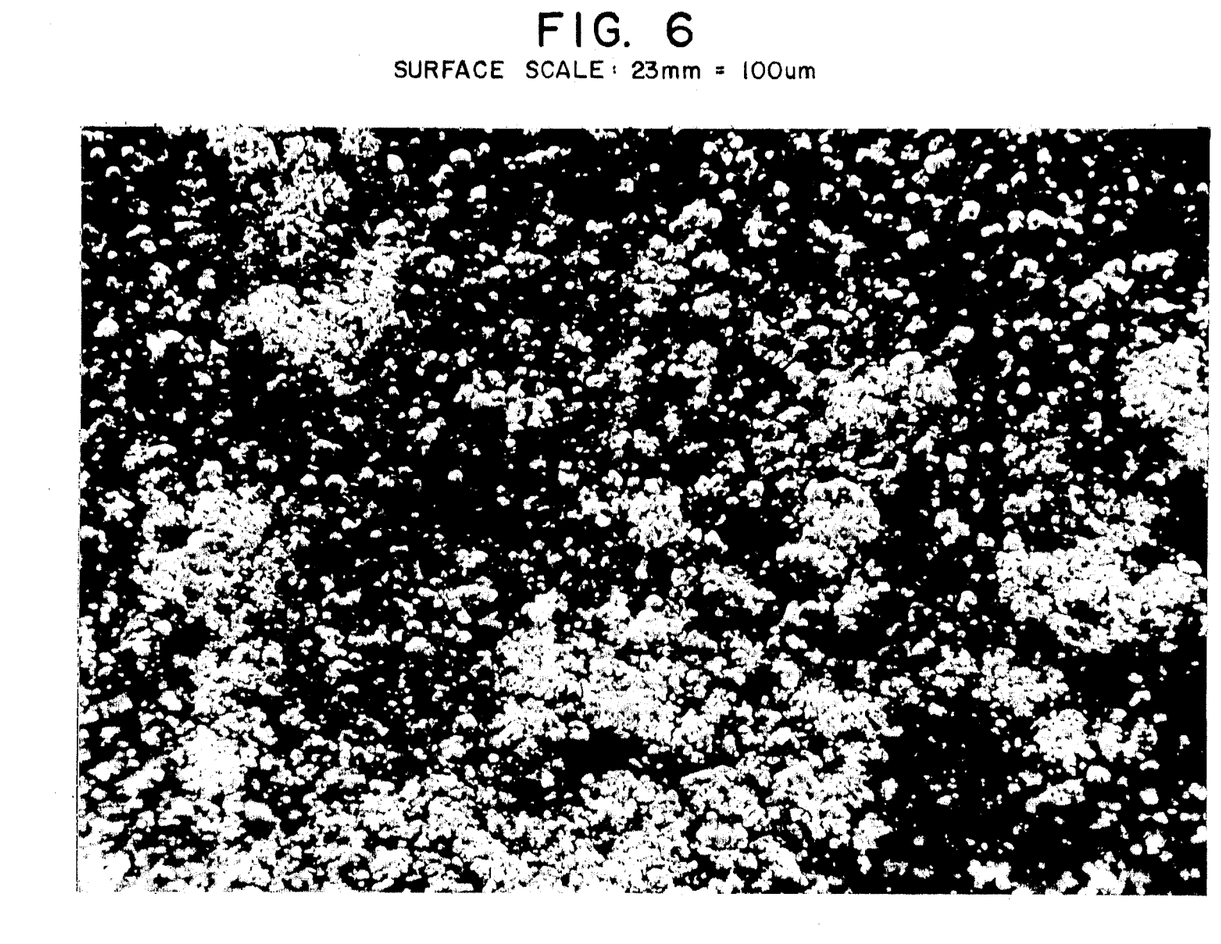
FIG. 6 is the same type of photomicrograph as FIG. 1 showing a coating finish similar to that of FIG. 1 on a natural rubber substrate.

As can be seen from the above Table, softer binders (i.e. binders with lower Tg) are needed to accomplish the same adhesion when a natural rubber substrate is used. FIG. 6 illustrates the adhesion and appearance of a glove according to Ex. 16. It can be seen that the finish is equivalent to that of Example 1. However, much harder binders are perfectly acceptable on polyurethane substrates: see below. Adhesion was measured as described above with 1 being excellent and 5 being the worst.

EXAMPLE 17

Comparison Example

A glove was made from natural rubber latex by the method described in Examples 15–16 except that the coating was that of Example 14 (U.S. Pat. No. 4,143,109). The adhesion of this coating in the finished glove was marginally better (rated 4.5) than that of Example 14 but the slip properties and appearance were the same.

EXAMPLE 18

Aqueous Phase

A glove was made from a polyurethane emulsion (Witcobond 787) by the general method described in Examples 15 and 16, dipping the wet gel into the coating dispersion described in Example 1. The adhesion of the coating was rated 1 and dry slip was rated 1.

EXAMPLES 1A, 7A, 8A–13A AND 19

The procedures of Examples 1 and 8–13 were repeated except as specified below:

Mean diameter was measured both as a weight percentage basis and on a volume percentage basis. In addition, the particle distribution was measured, using the Malvern apparatus. Finally, precipitated silica particles HK 125/400 were added to the materials tested. This material was tested by the procedure of Example 1 except that the coating contained 1.5% HK 125/400; 2.0% Aquaslip 671 polyethylene emulsion containing 40% solids 4.5% V3692 (50% solids), 0.2% xanthan gum; about 1% Dehydol TA 20 (20% solids) in 8 liters of deionized water. This material gave good adhesion (2) to the polyurethane substrate.

The results are set forth in Table 2A. The mean diameters (weight basis) are reproduced from Table 2. The mean diameters (volume basis) are the values preferred by the inventor and are consistent with the results obtained.

Figure 8:
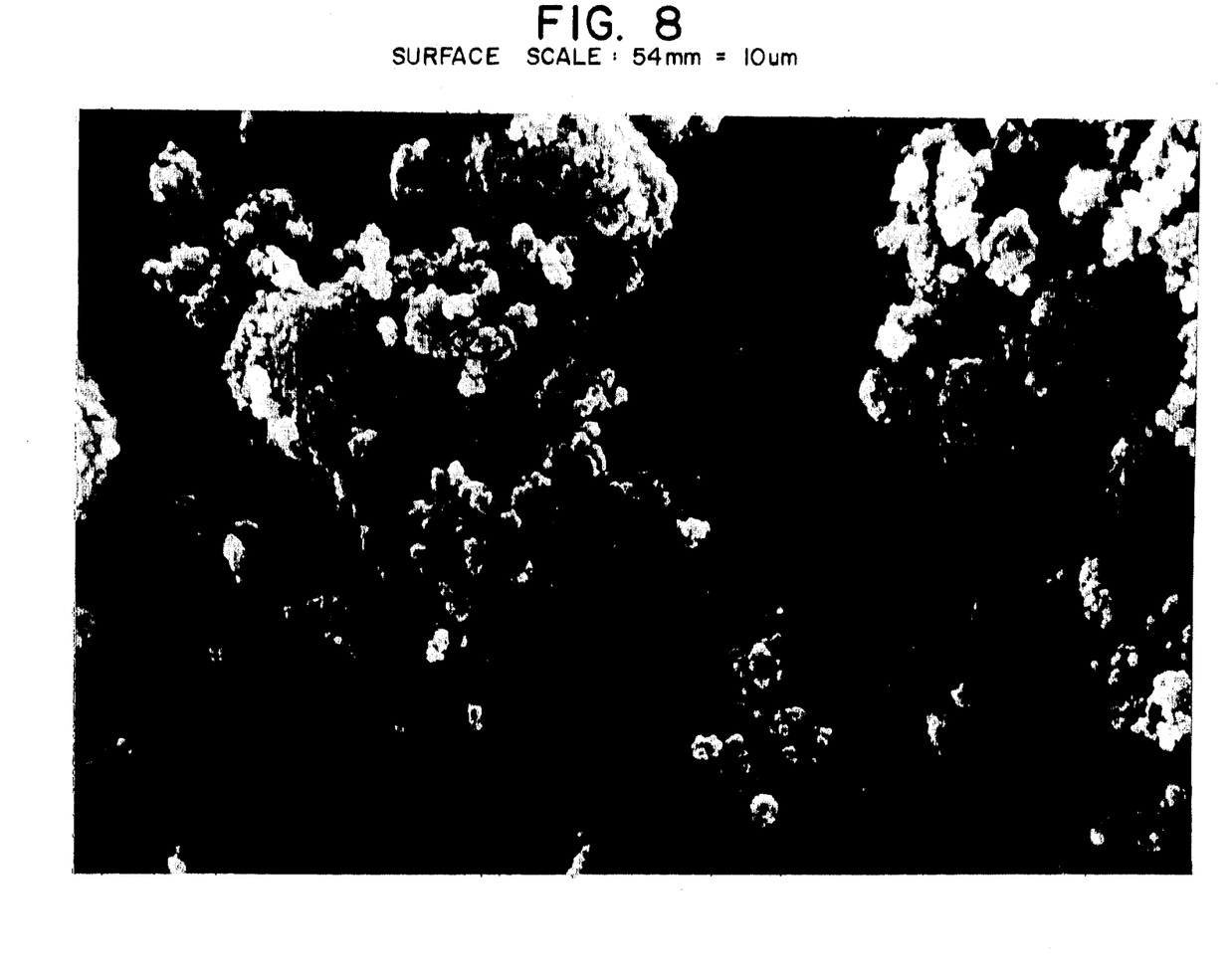

In a separate experiment, Syloid 622 produced good adhesion and a dry slip of "1" on a natural rubber substrate. The foregoing results yield the following conclusions:

Oil absorption should be fairly high (at least over 80/100 and preferably over 100/100). A narrow particle size distribution is preferred, the narrower the better. More important than the distribution is the use of nonaggregated particles which is a preferred feature of the invention: FK 383 and HK 125/400 are both aggregated particles made up of smaller (10–30 nm) primary particles as shown in FIGS. 7 and 8 respectively (compare with FIG. 1 which shows Syloid ED5 in the coating).

Stability of the dispersion in the binder is also a factor, as illustrated in Example 21 below.

TABLE 2A
EFFECT OF VARIOUS MICROPARTICLES ON PROPERTIES OF POLYURETHANE GLOVES

| Example Number | Particle Designation | Manufacturer | Mean Particle Diameter (microns) and Distribution (Volume %) | | | | Oil Absorption | Pore Volume (ml/g) | Dry Slip on Polyurethane |
|---|---|---|---|---|---|---|---|---|---|
| | | | Measured by Coulter (wt. %) | Measured by Malvern (vol. %) | in 4–20 micron range | in 5–13 micron range | | | |
| 1A | Syloid ED5 | Grace | 5µ | 8.8µ | 87% | 61% | 308 | 1.8 | 1 |
| 7A | Syloid ED80 | Grace | 8 | 11.1 | 75 | 45 | 300 | 1.8 | 1 |
| 8A | Syloid 622 | Grace | 12 | 12.8 | 59 | 33 | 180 | 1.2 | 1.5 |
| 9A | Syloid ED2 | Grace | 2 | 4.2 | 54 | 26 | 320 | 1.8 | 2.5 |
| 10A | FK 383 | Degussa | 1–2 | 7.6 | 57 | 37 | 230 | N/A | 3 |
| 11A | Syloid AL1 | Grace | 8 | N/A | N/A | N/A | 80 | 0.4 | 3 |
| 12A | Sipernat 50S | Degussa | 8 | 19.8 | 47 | 26 | 326 | N/A | 3.5 |

TABLE 2A-continued

EFFECT OF VARIOUS MICROPARTICLES ON PROPERTIES OF POLYURETHANE GLOVES

| Example Number | Particle Designation | Manufacturer | Mean Particle Diameter (microns) and Distribution (Volume %) | | | | Oil Absorption | Pore Volume (ml/g) | Dry Slip on Polyurethane |
|---|---|---|---|---|---|---|---|---|---|
| | | | Measured by Coulter (wt. %) | Measured by Malvern (vol. %) | in 4-20 micron range | in 5-13 micron range | | | |
| 13A | Corn Starch (non-cross-linked) | Biosorb | 5-40 | 14.4 | 75 | 28 | 58 | N/A | 2-3 |
| 19 | HK 125/400 | Degussa | N/A | 9.6 | 85 | 55 | 220 | N/A | 2 |

EXAMPLE 20

EFFECT OF DIFFERENT SUBSTRATES

Three alternative substrates to natural rubber and polyurethane were tested with a particularly preferred coating for adhesion and dry slip: Witcobond 769 Aqueous Polyurethane; Doverstrand 76D41 self cross-linking styrene-butadiene latex; and Shell Kraton D1117 styrene-isoprene-styrene block co-polymer in tetrahydrofuran.

These materials were cast onto glass plates using a K bar and partially dried (15–30 mins at 70° C.). The films, whilst still firmly adhered to the glass plate, were then dipped into the following coating formulation:
  0.5% Solid wax (A671)
  1.5% Silica (EDS)
  4.0% Solid binder (V3692)
  0.25% Xanthan Gum
  1.0% Solid Dehydol TA 20
  0.9% DC 193 silicone surfactants
The coated films were then dried for 30 min at 100° C. The films were stripped from the plate with the aid of water and coating quality/adhesion was assessed visually. The results are in Table 4.

TABLE 4

| EFFECT OF DIFFERING SUBSTRATES ON COATING ADHESION/SLIP | | |
|---|---|---|
| | Adhesion | Dry Slip |
| Witcobond 769 | Good | 1 |
| Doverstrand 76D41 | Good | 1 |
| Kraton D1117 | Good | 1 |

As can be seen all performed well and would be suitable as alternative substrates. Adhesion testing was visual and a "good" rating roughly corresponds to 2 in Table 1. Coating quality and dry slip properties were similar to those obtained on polyurethane.

EXAMPLE 21

FURTHER PARTICLE EVALUATION

The following additional particles were tested for oil absorption as described. The results are summarized in Table 5:

TABLE 5

| OIL ABSORPTION OF VARIOUS PARTICLES | |
|---|---|
| Particle | Oil Absorption g/100 g |
| Non-crosslinked Corn Starch | 40 |
| Microthene (FN510) | 50 |
| Microthene FE 532 | 51 |
| Magnesium oxide | 140 |
| Aluminum oxide | 34 |
| Orgasol 2002 UD | 120 |

TABLE 5-continued

| OIL ABSORPTION OF VARIOUS PARTICLES | |
|---|---|
| Particle | Oil Absorption g/100 g |
| Orgasol 2002 EXD | 100 |
| Celluflow TA25 | 115 |

The particles with high oil absorption values were then assessed for mean size (% volume) and proportion (% volume) between 3 and 20 μm, and between 4 and 12 μm. The results are in Table 6.

TABLE 6

| | Particle Size Distribution Data As Measured by Malvern Instruments | | | |
|---|---|---|---|---|
| Particle | Mean Particle Size μm | Proportion between 3 and 20 μm (%) | Proportion between 4-12 μm (%) | Span * |
| Magnesium oxide | 4.9 | 76 | 55 | 1.68 |
| Aluminum oxide | 4.6 | 69 | 50 | 2.04 |
| Polyamide powder (Orgasol 2002 UD) | 4.8 | 74 | 50 | 1.68 |
| Polyamide powder (Orgasol 2002 EXD) | 10.2 | 78 | 58 | 1.86 |
| Cellulose triacetate (TA25) | 12.2 | 78 | 38 | 1.53 |

*Span is an arbitrary measure shown on the Malvern printouts which gives an indication to the breadth of particle size distribution. For wide distributions the number is large and conversely for small distributions the number is small.

The particles with appropriate mean size and oil absorption were further evaluated as follows:
a)
  13 g Magnesium oxide dispersed in 400 g deionized water using a paddle stirrer.
  2 g Xanthan gum dispersed in 400 g deionized water using a Silverson mixer.
  These mixtures were then blended together by gentle stirring. To this dispersion was added 78 g of Vinamul V3692 (binder) and this dispersion was stirred thoroughly. The formulation was made up to 1L using deionized water. This dispersion was then consigned to a measuring cylinder ready for dipping. Dispersion stability was checked visually immediately after formulation and then again 24 hrs later.
  This formulation process was repeated with the following powders and with the following exceptions:

Magnesium Oxide. Ammoniated water and Beetle 9040 (binder) were used to increase pH to match the pH of MgO in dispersion.

Aluminum Oxide

Cellulose triacetate (TA25) 2 g of Laurapal X1207 added to aid with dispersion of powder in deionized water. Silverson mixer used.

Polyamide (Orgasol 2002 UD): 2 g of Laurapal X1207 added to aid dispersion of powder in deionized water. V3231 binder used since the dispersion was intended for use with natural rubber latex. Silverson mixer used.

All of these dispersions were dipped on to 'wet gel' thermoplastic polyurethane as in Example 1. However, condom formers were used and for the final example (Orgasol 2002 EXD) the substrate used was natural rubber latex—again in a wet gel state. The condoms were then processed as per the gloves in Example 1.

The resultant condoms were assessed visually for adhesion of coating to substrate, surface-to-surface dry slip, and dry slip against the skin.

The results are described in Table 7:

The Kraton G was dispersed in 2200 g of Toluene using a paddle stirrer. This process was repeated with the crepe rubber and the starch. The three mixtures were then blended together in a 8-L dipping pot. The dispersion was covered and left to stand overnight before dipping commenced. The dispersion was stirred vigorously immediately before dipping.

| (2) Second Comparative Formulation (U.S. Pat. No. 4,143,109) | |
|---|---|
| 300 g | Brominated butyl rubber (solid) |
| 10.5 g | Stearic acid |
| 3.75 g | Antioxidant 2246 (2,2'-Methylene bis (-4 methyl-6-t-butyl phenol) |
| 15.0 g | Paraffin wax |
| 75.0 g | Finely divided talc |
| 6.0 g | Petroleum jelly |
| 6.0 | Titanium dioxide |
| 15.0 g | Zinc oxide |
| 3.0 g | Zinc dimethyldithiocarbamate |
| 375 g | Microthene FN 510 polyethylene |
| 7500 g | Hexane |
| 8309.25 g | Total (represents approx. 1:1 particle:binder ratio) |

TABLE 7

STABILITY OF DISPERSIONS AND COATING CHARACTERISTICS

| FORMULATION | STABILITY 0 HRS | STABILITY 24 HRS | ADHESION TO SUBSTRATE | SLIP PROPERTIES | 'FEEL' |
|---|---|---|---|---|---|
| Magnesium oxide | Flocculated | Flocculated | Generally good but poorer in aggregated areas | Acceptable (2.5) | Very granular, grainy |
| Magnesium oxide (high ph) | Flocculated | Flocculated | | | |
| Aluminum oxide | O.K. | Settling | Poor wetting | Inconsistent: some drag. Barely acceptable (3) | Feels powdery |
| Orgasol 2002 UD | O.K. | O.K. | Excellent | Excellent (1) | Similar to ED5 system but slightly smoother |
| 2002 EXD/V3231 on natural rubber | O.K. | O.K. | Excellent | Excellent (1) | As 2002 UD |
| TA25 | O.K. | O.K. | Good/ excellent | Excellent (1) | Slightly papery |
| Ex. 22 (1) | O.K. | Settled | Coverage very patchy. Flakes off, particularly when wet | Poor and 'draggy' (4) | Very granular and distinctly rough |
| Ex. 22 (2) | O.K. | Settled | Better coverage than Ex. 22 (2) but can be easily abraded. | Poor (3-4) | very granular and rough |

The best performances in terms of adhesion and slip properties were those of polyamide powders and cellulose triacetate. Magnesium and aluminum oxide showed poor dispersion stability which probably accounts for the poor properties of coatings containing them.

EXAMPLE 22

COMPARATIVE EXAMPLE

In addition, as comparative examples the following glove coating formulations and gloves were made:

| (1) First Comparative Formulation (U.S. Pat. No. 4,143,109) | |
|---|---|
| 300 g | Kraton G 1650 (SEBS) |
| 30 g | Pale crepe grade of natural rubber |
| 300 g | White mineral oil |
| 6600 g | Toluene |
| 300 g | Crosslinked corn starch |
| 7530 g | Total (represents approx 1:1 particle:binder ratio) |

The brominated butyl rubber latex was dried down to form brominated butyl rubber and subsequently cut into very small pieces before dissolution in 2000 g of hexane. To this solution were added petroleum jelly and paraffin wax. A clear solution without lumps or gels was formed. The remaining ingredients (except the Microthene) were dispersed in 200 g of hexane then blended into the solution. After further stirring Microthene beads were dispersed into the remaining hexane before being blended with the bulk solution. After a further period of stirring the dispersion was placed in an appropriate dip pot and covered. The dispersion was left to stand before dipping commenced; however the dispersion was stirred immediately prior to dipping.

Both comparative materials were examined for dispersion stability immediately and 24 hrs after mixing. These dispersions were applied to glove formers coated with a thermoplastic polyester polyurethane. The polyester polyurethane had been dried for 30 mins at ambient temperature after dipping from an approximate 18% solution in tetrahydrofuran. The gloves were subsequently dried at 100° C. for 30 mins before hydration and stripping. The gloves were then visually examined and donned to assess the slip qualities.

The results are also shown in Table 7.

Neither of the examples taken from U.S. Pat. No. 4,143,109 provided an acceptable slip coating. The particles were not well bonded to the substrate, probably because they did not absorb the binder adequately (low oil absorption). The surfaces they provided were granular and showed poor slip. This is ascribed to the relatively large size of the particles (described by the manufacture as having a mean diameter of about 20 micron).

What is claimed is:

1. A flexible article displaying slip properties with respect to damp and dry mammalian tissue without use of powder lubricants comprising:

a substrate layer comprising an elastomeric material, said layer having a wearer-contacting surface, said surface having a dry slip conferring coating bonded to said elastomeric material said coating comprising (i) a binder and (ii) absorbent substantially nonaggregated microparticles, said microparticles having an average diameter within the range from about 4 to about 20 microns, an oil absorption higher than about 80 g of oil per 100 g of said microparticles, said microparticles being enveloped by said binder but partially protruding therefrom thus imparting to said surface a microroughened appearance; and a damp slip-conferring amount of a surfactant applied to said wearer-contacting surface.

2. The article of claim 1 wherein said microparticles have a pore volume higher than 1 ml/g.

3. The article of claim 2 wherein said microparticles are made of silica.

4. The article of claim 1 wherein said coating has a thickness that does not exceed about 5% of the thickness of said substrate.

5. The article of claim 4 wherein said microparticles are substantially regular in shape.

6. The article of claim 4 wherein said microparticles are made of silica.

7. The article of claim 1 wherein at least about 55% of the microparticles have a diameter within said range.

8. The article of claim 1 wherein the weight ratio of said binder to said particles is greater than 1:1 and smaller than about 5:1.

9. The article of claim 1 wherein said elastomer is selected from the group consisting of natural rubber, a polyurethane, a polyacrylate, a polybutylene, a silicone rubber, and a block copolymer of styrene and butadiene.

10. The article of claim 6 wherein said binder is a polymer having a glass transition temperature higher than −60° and lower than +30°.

11. The article of claim 1 wherein said binder is selected from the group consisting of nonwater-sensitive copolymers and terpolymers of vinyl acetate with at least one of ethylene, ethylene acrylate and vinyl chloride.

12. The article of claim 1, said article being a medical glove.

13. The article of claim 1, said microparticles having a mean diameter within the range of 5–13 microns.

14. The article of claim 1, said surfactant comprising an amphoteric surfactant.

15. The article of claim 14, said surfactant being an alkyldimethylammonium betaine.

16. The article of claim 1, said surfactant being a cationic surfactant.

17. An article according to claim 16, in which said surfactant is a quaternary ammonium compound having at least one $C_6$–$C_{18}$ hydrocarbyl group.

18. An article according to claim 17, in which said hydrocarbyl group is attached to a quaternary nitrogen atom which is part of a heterocyclic ring.

19. An article according to claim 18, in which the heterocyclic ring is pyridine, morpholine or imidazoline.

20. An article according to claim 19, in which the surfactant is an N-lauryl or N-cetyl pyridinium salt, or a hydroxyethyl heptadecenyl imidazoline salt.

21. An article according to claim 17, in which said surfactant is hexadecyl trimethyl ammonium chloride.

22. An article according to claim 17, in which said surfactant is benzalkonium chloride.

23. An article according to claim 17, in which said surfactant is hexadecyl pyridinium chloride.

24. The article of claim 1, said oil absorption being higher than 180 g of oil per 100 g microparticles.

25. The article of claim 9 wherein said polyurethane is selected from the group of polyethers, polyesters, polycaprolactones, and combinations of at least two of the foregoing.

26. A flexible article displaying slip properties with respect to damp and dry mammalian tissue without the use of powder lubricants, said tissue including skin, said article comprising:

a substrate layer comprising a polyurethane elastomer, said layer having a tissue-contacting surface, said surface having a coating bonded thereto, said coating (i) having a thickness not exceeding about 5% of the thickness of said substrate and (ii) comprising an elastomeric binder having a glass transition temperature within the range of −60° to +15° C., said binder enveloping porous silica primary microspheres having a mean diameter within the range of about 5 to about 13 microns, an oil absorption at least 100 g of oil per 100 g of said particles, said microspheres partially protruding from said binder and imparting to said tissue-contacting surface a microroughened appearance and thereby conferring dry-slip properties to said surface; and a damp slip-conferring amount of a surfactant applied to said coated wearer-contacting surface, said damp and dry slip properties making the surface lubricous with respect to damp and dry tissue without the use of other lubricants.

27. The article of claim 26, said surfactant being selected from the group consisting of cationic and amphoteric surfactants.

28. The article of claim 26, said polyurethane being selected from the group of polyethers, polyesters, polycaprolactones, and combinations of at least two of the foregoing.

29. The article of claim 26, wherein at least 60% of said microspheres have a diameter within the range of about 5 to about 13 μm.

30. The article of claim 26, wherein said binder and said microparticles are present at a weight ratio greater than 1:1 and smaller than about 5:1.

31. A flexible article displaying slip properties with respect to damp and dry mammalian tissue without use of powder lubricants comprising:

a substrate layer comprising an elastomeric material, said layer having a wearer-contacting surface, said surface having a dry slip conferring coating bonded to said elastomeric material said coating comprising (i) a binder and (ii) absorbent substantially nonaggregated microparticles, said microparticles having an average diameter within the range from about 4 to about 20 microns, an oil absorption higher than about 80 g of oil per 100 g of said microparticles; and a damp slip-conferring amount of a surfactant applied to said wearer-contacting surface.

32. The article of claim 31, wherein the weight ratio of said binder to said microparticles is greater than 1:1 and smaller than about 5:1.

33. The article of claim 32, wherein said coating has a thickness that does not exceed about 5% of the thickness of said substrate.

34. The article of claim 33, wherein at least about 55% of the microparticles have a diameter within said range.

35. The article of claim 34, wherein at least 30% of said microparticles have a diameter within the range of about 5 to about 13 microns.

36. The article of claim 35, wherein the oil absorption is at least 100 g of oil per 100 g of said microparticles.

37. A flexible article displaying slip properties with respect to damp and dry mammalian tissue without use of powder lubricants comprising:

a substrate layer comprising an elastomeric material, said layer having a wearer-contacting surface, said surface having a dry slip conferring coating bonded to said elastomeric material said coating comprising (i) a binder and (ii) absorbent microparticles, said microparticles having an oil absorption higher than about 80 g of oil per 100 g of said microparticles; and a damp slip-conferring amount of a surfactant applied to said wearer-contacting surface.

* * * * *